United States Patent
Pollak et al.

[11] Patent Number: 5,976,497
[45] Date of Patent: Nov. 2, 1999

[54] DOPAMINE D4 RECEPTOR LIGANDS

[75] Inventors: Alfred Pollak, Toronto; Robert Dunn-Dufault, Guelph; David Roe, Rockwood, all of Canada

[73] Assignee: Resolution Pharmaceuticals, Inc., Ontario, Canada

[21] Appl. No.: 08/905,546

[22] Filed: Aug. 4, 1997

[51] Int. Cl.$^6$ ................................... A61K 49/00
[52] U.S. Cl. .................. 424/1.85; 424/1.89; 514/255; 544/362
[58] Field of Search ............. 544/362; 514/255; 424/1.85, 1.89

[56] References Cited

U.S. PATENT DOCUMENTS

| | | | |
|---|---|---|---|
| 3,362,956 | 1/1968 | Archer | 260/268 |
| 3,511,841 | 5/1970 | Archer | 260/268 |
| 5,219,860 | 6/1993 | Chambers et al. | 514/278 |
| 5,304,367 | 4/1994 | Biegon | 424/1.11 |
| 5,324,733 | 6/1994 | Billington et al. | 514/278 |
| 5,372,813 | 12/1994 | Mathis, Jr. et al. | 424/1.85 |
| 5,432,177 | 7/1995 | Baker et al. | 514/253 |
| 5,576,319 | 11/1996 | Baker et al. | 514/249 |
| 5,622,950 | 4/1997 | Baker et al. | 514/253 |

FOREIGN PATENT DOCUMENTS

| | | | |
|---|---|---|---|
| WO 94/20497 | 9/1994 | WIPO | C07D 471/04 |
| WO 97/19073 | 5/1997 | WIPO | C07D 401/14 |

OTHER PUBLICATIONS

Kulagowski et al, J Med Chem, 1996, 39:1941 "3-[[4-4-(Chlorophenyl)piperazin-1-yl]methyl]-1H-pyrrolo[2,3-b]pyridine: An Antagonist with High Affinity and Selectivity for the Human Dopamine D4 Receptor".

Kung et al, Society for Neurosciences Abstracts, vol. 22, Part 2, Abstract No. 330.5, p. 828, presented at the 26th Annual Meeting of the Society for Neurosciences, Nov. 16–21, 1996, Washington, D.C.. "Binding Characteristics of Iodinated Ligands for Dopamine D4 Receptors".

Patel et al, Molecular Pharmacology, 1996, 50:1158–1664 "Identification and Pharmacological Characterization of [$^{125}$I]L–750, 667, a Novel Radioligand for the Dopamine D$_4$ Receptor".

Chavez–Eng et al, Journal of Chromatography B, 1997, vol. 691, pp. 77–85 "Picogram Determination of a Novel Dopamine D$_4$ Receptor Antagonist in Human Plasma and Urine by Liquid Chromatography with Atmospheric Pressure Chemical Ionization Tandam Mass Spectrometry".

Kung et al, Life Sciences, 1997, vol. 60, No. 2, pp. 91–100 "Characterization of a Novel Iodinated Ligand, IPMPP, for Human Dopamine D$_4$ Receptors Expressed in CHO Cells".

Patel et al, Life Science News, Nov. 1996, Issue 21, pp. 21 "[$^{125}$I]L–750, 667, a Novel Radioligand for the Dopamine D$_4$ Receptor".

Primary Examiner—Richard L. Raymond
Attorney, Agent, or Firm—Nikaido Marmelstein Murray & Oram, LLP

[57] ABSTRACT

Described herein are D4 receptor-selective compounds of the formula:

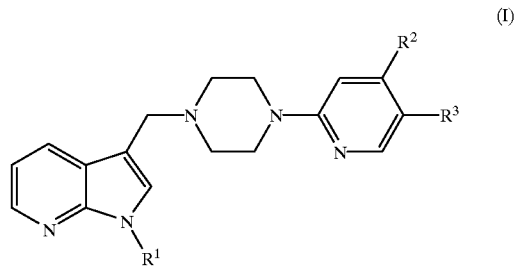

(I)

wherein $R^1$ is selected from H and an acid labile protecting group; and $R^2$ and $R^3$ are independently selected from H, radioisotopic halo, loweralkoxy and tri(loweralkyl)tin; and salts, solvates or hydrates thereof.

Also described is the use of these compounds as pharmaceuticals to treat indications for which a dopamine D4 receptor antagonist is indicated. Radiolabeled compounds are useful particularly to image localization of D4 receptor in the human brain, and can therefore aid in the diagnosis of schizophrenia and other medical conditions in which the D4 receptor is implicated.

2 Claims, No Drawings

DOPAMINE D4 RECEPTOR LIGANDS

This invention relates to compounds that bind to the dopamine D4 receptor, and to their use for therapeutic and diagnostic purposes.

BACKGROUND OF THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et al, Nature, 1993, 365:441). Some dopamine receptor ligands currently sold as pharmaceuticals exhibit the desired affinity and antagonism for the D4 receptor, yet interact non-selectively with related dopamine receptors, particularly the D2 receptor type, which results in significant side effects that include altered motor function and tachycardia. It would be desirable to provide compounds that exhibit not only a high degree of affinity for the D4 receptor, but also a relatively low degree of affinity for the D2 receptor. In this specification, this desired combination of receptor binding properties is referred to as D4 selectivity.

Products currently marketed to treat indications in which the D4 receptor function is implicated include the dibenzodiazepine, clozapine, and the dibenzoxazepine, isoloxapine. Analysis of their dopamine receptor binding properties has shown that the preference for binding to the D4 receptor relative to the D2 receptor is about 10 fold, for both products. Similarly, both bind to the D4 receptor with about the same affinity (Ki value approximately 20 nM). More recently, selective D4 receptor antagonists have been identified among other classes of compounds (see, for example, Baker et al. U.S. Pat. No. 5,576,336 issued Nov. 19, 1996; Baker et al. U.S. Pat. No. 5,622,950 issued Apr. 22, 1997; and Baker et al. U.S. Pat. No. 5,432,177 issued Jul. 11,1995).

In the context of medical diagnostics, this non-selective binding at the D4 receptor prevents the generation of an accurate image of the localization and prevalence specifically of the D4 type of dopamine receptor. It would therefore be desirable to provide compounds that, in their radiolabeled state, bind at the D4 receptor with affinity and selectivity appropriate for diagnostic imaging purposes. When used in combination with such diagnostic imaging techniques as single photon emission tomography (SPECT) and positron emission tomography (PET), such radiolabeled compounds would be useful particularly to diagnose schizophrenia and other medical conditions associated with D4 receptor anomalies.

SUMMARY OF THE INVENTION

According to one aspect of the present invention, there are provided compounds of Formula (I):

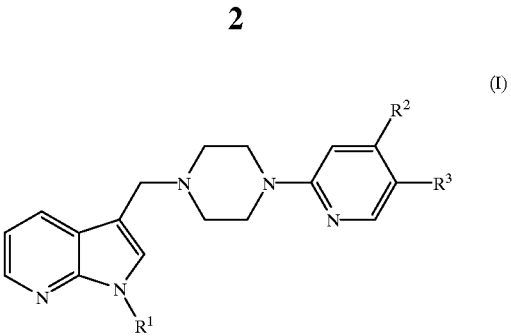

wherein $R^1$ is selected from H and an acid labile protecting group; and $R^2$ and $R^3$ are independently selected from H, radioisotopic halo, loweralkoxy and tri(loweralkyl)tin; and salts, solvates or hydrates thereof.

According to another aspect of the invention, there is provided a pharmaceutical composition comprising a compound of Formula (I) wherein $R^2$ and $R^3$ are H, in an amount effective to antagonize D4 receptor stimulation and a pharmaceutically acceptable carrier.

In another of its aspects, the invention provides the use of compounds of Formula (I) as D4 receptor antagonists for the treatment of medical conditions mediated by D4 receptor stimulation.

According to another aspect of the invention, there is provided a radiopharmaceutical composition comprising a compound of Formula (I) wherein one of $R^2$ and $R^3$ is a radioisotopic halo and $R^1$ is H, and a pharmaceutically acceptable carrier such as physiological buffered saline.

In a further aspect of the invention, there is provided a method for imaging D4 receptors in vivo, comprising the step of administering systemically to a patient an effective amount of a radiopharmaceutical composition comprising a compound of Formula (I) wherein one of $R^2$ and $R^3$ is a radioisotopic halo and $R^1$ is H and a pharmaceutically acceptable carrier, allowing the radiopharmaceutical to localize within the brain, and then taking an image of the brain of the patient so treated.

DETAILED DESCRIPTION OF THE INVENTION

The term 'loweralkyl' as used herein means straight chain alkyl radicals containing a from one to six carbon atoms and branched chain alkyl radicals containing three to six carbon atoms and includes methyl, n-butyl, 1-methylethyl and the like.

The term 'alkoxycarbonyl' as used herein means straight and branched chain alkyl carbonates containing from two to six carbon atoms and includes methoxycarbonyl, ethoxycarbonyl, t-butoxycarbonyl and the like.

The term 'halo' as used herein means a halogen radical selected from bromo, chloro, fluoro or iodo. Radioisotopic halo include $^{123}$I, $^{125}$I, $^{131}$I, $^{18}$F, and $^{76}$Br.

The term acid labile protecting group as used herein means a protecting group that affords protection to the functional group to which it is attached from undesired attack yet is cleavable from the molecule under acidic conditions. Suitable acid labile protecting groups are disclosed in, for example, T. W. Greene and P. G. M. Wuts, *Protective Groups in Organic Synthesis,* 2nd Edition, 1991, John Wiley & Sons Inc., New York, and include groups such as t-butoxycarbonyl.

Compounds of the present invention are those of Formula (I) in which $R^1$, $R^2$ and $R^3$ are as defined above.

A preferred group of compounds of this invention are represented by Formula (I) wherein $R^1$ is selected from H, alkoxycarbonyl and alkoxyalkyl, and $R^2$ and $R^3$ are independently selected from H, radioisotopically labeled halo, loweralkoxy, tributyltin and trimethyltin.

A more preferred group of compounds of this invention is represented by Formula (I) wherein $R^1$ is selected from H, t-butoxycarbonyl and methoxymethyl, and $R^2$ and $R^3$ are independently selected from H, $^{123}$I, $^{125}$I, $^{131}$I, $^{18}$F, tributyltin, trimethyltin and methoxy.

A most preferred group of compounds of this invention are represented by Formula (I) wherein $R^1$ is selected from H and t-butoxycarbonyl, and $R^2$ and $R^3$ are independently selected from H, I, Br, $^{123}$I and trimethyltin.

Acid addition salts of the compound of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

Compounds of Formula (I), wherein $R^1$ is H and one of $R^2$ and $R^3$ is a radioisotopically labeled iodide, can be prepared by reacting compounds of Formula (I), wherein one of $R^2$ and $R^3$ is tri(loweralkyl)tin and $R^1$ is H, with radioisotopic iodide source, for example a solution of radioisotopically labeled sodium iodide (e.g. as a solution in 1N NaOH), in the presence of an acid and an oxidizing agent in an alcoholic solvent. Preferred conditions are Chloramine T and hydrochloric acid in ethanol.

In a preferred method, compounds of Formula (I), wherein $R^1$ is H and one of $R^2$ and $R^3$ is a radioisotopic iodide, are prepared by reacting a compound of Formula (I), wherein one of $R^2$ and $R^3$ is tri(loweralkyl)tin and $R^1$ is alkoxycarbonyl, with a radioisotopic iodide source as described above, followed by removal of the alkoxycarbonyl protecting group under acidic conditions in the same reaction vessel. The preferred acid is hydrochloric acid.

To generate compounds of the Formula (I) wherein $R^1$ is H and $R^2$ and $R^3$ are as described above, an appropriately substituted piperazine is coupled with 1H-pyrrolo[2,3-b]pyridine in the presence of formaldehyde in an aqueous buffer solution, for example aqueous sodium acetate in acetic acid. The 1H-pyrrolo[2,3-b]pyridine is commercially available and the piperazines are either commercially available or can be prepared by one skilled in the art. Thus 1-(pyridin-2-yl)piperazine is coupled with 1H-pyrrolo[2,3-b]pyridine in the presence of formaldehyde in a buffer made up of sodium acetate and acetic acid. The substituted piperazines are prepared by reaction of an appropriately substituted pyridine with piperazine in the presence of a base in an inert solvent such as acetonitrile, at temperatures between 0 and 100° C., preferably at reflux. Suitable bases include piperazine itself, sodium or potassium carbonate.

Compounds of the Formula (I) wherein $R^1$ is H and $R^2$ and $R^3$ are as described can also be prepared by treatment of an appropriately substituted piperazine with 3-(N,N-dimethylaminomethyl)-1H-pyrrolo[2,3-b]pyridine in a suitable inert solvent, preferably toluene, at a temperature between 50–120° C. preferably at reflux. Thus 1-(5-iodopyridin-2-yl)piperazine is coupled with 1H-pyrrolo[2,3-b]pyridine in toluene at reflux.

Compounds of Formula (I) wherein $R^1$ is alkoxycarbonyl and $R^2$ and $R^3$ are as described above can be prepared by reacting compounds of Formula (I) wherein $R^1$ is H and $R^2$ and $R^3$ are as described above with dialkoxydicarbonate reagents in the presence of a base in an inert solvent at temperatures in the range of 0–50° C., preferably at around room temperature. Suitable bases include sodium or potassium hydroxide or triethylamine. Suitable inert solvents include chloroform, dichloromethane or acetonitrile. Preferred conditions are potassium hydroxide in dichloromethane. The dialkoxydicarbonate reagents are readily available protecting group reagents.

Compounds of Formula (I) wherein $R^1$ is alkoxycarbonyl and $R^2$ or $R^3$ are tri(loweralkyl)tin can also be prepared by reacting compounds of Formula (I) wherein $R^1$ is alkoxycarbonyl and R2 or $R^3$ is iodo with hexa(loweralkyl)ditin reagents under standard palladium catalyzed cross-coupling conditions, for example, in the presence of a catalytic amount of tetrakis(triphenylphosphine)palladium (0) in an inert solvent, for example, toluene at temperatures ranging from 50–120° C. preferably at about 110° C.

In preferred embodiments of the invention, the compounds are selected from:
  3-[4-(5-iodopyridin-2-yl)-piperazin-1-yl]methyl-1H-pyrrolo[2,3-b]pyridine;
  1-t-butoxycarbonyl-3-[4-(5-trimethylstannylpyridin-2-yl)piperazin-1-yl]methyl-1H-pyrrolo[2,3-b]pyridine;
  3-[4-(pyridin-2-yl)piperazin-1-yl]methyl-1H-pyrrolo[2,3-b]pyridine;
  3-[4-(5-bromopyridin-2-yl)piperazin-1-yl]methyl-1H-pyrrolo[2,3-b]pyridine; and 1-t-butoxycarbonyl-3-[4-(5-bromopyridin-2-yl)-piperazin-1-yl]methyl-1H-pyrrolo[2,3-b]pyridine.

In more preferred embodiments of the invention, the compounds are selected from:
  3-[4-(5-iodopyridin-2-yl)-piperazin-1-yl]methyl-1H-pyrrolo[2,3-b]pyridine; and 1-t-butoxycarbonyl-3-[4-(5-trimethylstannylpyridin-2-yl)-piperazin-1-yl]methyl-1H-pyrrolo[2,3-b]pyridine.

The compounds of the invention wherein $R^2$ or $R^3$ are radioisotopic iodide are formulated as radiopharmaceutical compositions together with any physiologically and radiologically tolerable vehicle appropriate for administering the compound systemically. Included among such vehicles are phosphate buffered saline solutions, buffered for example to pH 7.4.

For use in medicine, the compounds of the present invention can be administered in a standard pharmaceutical composition. The present invention therefore provides, in a further aspect, pharmaceutical compositions comprising a pharmaceutically acceptable carrier and a Formula (I) compound or a pharmaceutically acceptable salt, solvate or hydrate thereof, in an amount effective to antagonize D4 receptor stimulation.

The compounds of the present invention may be administered by any convenient route, for example by oral, parenteral, buccal, sublingual, nasal, rectal or transdermal administration and the pharmaceutical compositions formulated accordingly.

Compounds of Formula (I) and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alteratively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the conditions for which administration of a chosen compound is indicated and will of course vary depending on the desired clinical endpoint. It is anticipated that dosage sizes appropriate for administering the compounds of the examples will be roughly equivalent to, or slightly less than, those used currently for clozapine. Accordingly, each dosage unit for oral administration may contain from 1 to about 500 mgs, and will be administered in a frequency appropriate for initial and maintenance treatments.

For imaging and diagnostic purposes, it is contemplated that the present compounds will be administered to patients by intravenous injection or infusion at doses suitable (e.g. between 1 and 10 mCi) to generate an image of the compound as localized within the brain, using for example a gamma camera. Preferably, the compounds will be administered and allowed to localize within the brain for 30 minutes to 48 hours prior to generating an image of the brain of the patient so treated. It is further contemplated that the method of the present invention can usefully be applied diagnose to patients suspected of suffering from schizophrenia. For these patients, diagnosis can be aided or confirmed by determining the intensity of radiolabeled compound relative to the brain of a healthy patient; greater image intensity is indicative of an overabundance of D4 receptor, and is hence indicative of a schizophrenic condition.

EXAMPLE 1: Preparation of 3-[4-(pyridin-2-yl)-piperazin-1-yl]methyl-1H-pyrrolo[2,3-b]pyridine (a) 3-(N,N-Dimethylaminomethyl)-1H-pyrrolo[2,3-b]pyridine 7-azaindole (5.0 g, 17 mmole), dimethylammonium chloride (3.76 g), and paraformaldehyde (1.40 g) were dissolved in n-butanol (30 mL). The reaction was refluxed for 1 hour where upon cooling to room temperature fluffy white needles crystalized out. These were filtered and washed with butanol (10 mL). The solid was dried in vacuo to a white crystalline solid massing 6.1 g. A portion of this material (2.0 g) was converted to the free base by dissolving in 20 mL water. Upon the addition of ammonium hydroxide (aqueous, 30%) (2 mL) a white precipitate formed, was filtered, washed with water (5 mL), and dried in vacuo to yield 3-(N,N-dimethylaminomethyl)-1H-pyrrolo[2,3-b]pyridine (2.0 g, 27% yield). $\delta$H (300 MHz CDCl$_3$) 2.27 (6H, s), 3.61 (2H, s), 7.09 (1H, dd, J=4.5 and 8.0), 7.28 (1H, s), 8.04 (1H, dd, J=1.2 and 8.1), 8.32 (1H, dd, J=1.2 and 4.7), ESMS 176 (MH$^+$)

(b) 3-[4-(pyridin-2-yl)-piperazin-1-yl]methyl-1H-pyrrolo[2,3-b]pyridine

To a solution of 3-(N,N-dimethylaminomethyl)-1H-pyrrolo[2,3-b]pyridine (258 mg, 1.39 mmol) (prepared in Example 1(a)) in toluene (10 mL) was added 1-(pyridin-2-yl)piperazine (233 mL, 250 mg, 1.53 mmol). The mixture was heated at reflux over night. Heating was discontinued and when the reaction temperature had reached room temperature the solid was filtered off and dried in vacuo to give 3-[4-(pyridin-2-yl)-piperazin-1-yl]methyl-1H-pyrrolo[2,3-b]pyridine as a colourless solid (395 mg, 93%). $\delta$H (300 MHz, CDCl$_3$) 2.50 (4H, m, piperazinyl), 3.46 (4H, m, piperazinyl), 3.68 (2H, s), 6.61 (1H, dd, J=5.1 and 6.9), 6.78 (1H, d, J=8.6), 7.06 (1H, dd, J=4.7 and 7.8), 7.39 (1H, s), 7.51 (1H, dd, 6.9 and 8.6), 8.10 (1H, d, J=8.1), 8.12(1H, d, J=7.8), 8.22(1H, d, J=4.6),11.49(1H, br s); ESMS 294 (MH$^+$)

EXAMPLE 2: Preparation of 3-[4-(5-iodopyridin-2-yl)-piperazin-1-yl]methyl-1H-pyrrolo[2,3-b]pyridine (a) 2-Chloro-5-iodopyridine To a suspension of 5-amino-2-chloropyridine (2.56 g, 20 mmol) and hydriodic acid (57% solution in water, 6.8 mL) in dichloromethane (50 mL) at 0° C. was added NaNO$_2$ portionwise over 2 min. The reaction was then stirred at 0° C. for a further 30 min and then poured into a mixture of dichloromethane and saturated sodium thiosulphate solution and the organic layer separated. The aqueous layer was extracted further with dichloromethane (2×50 mL) and the combined organic extracts were dried over MgSO$_4$, filtered and the solvents removed under reduced pressure. Column chromatography of the residue on silica gel (dichloromethane as eluent) gave 2-chloro-5-iodopyridine as a colourless solid (930 mg, 20%). $\delta$H (300 MHz, CDCl$_3$) 7.10 (1H, d, J=8.3), 7.88 (1H, dd, J=2.4 and 8.2), 8.55 (1H, d, J=2.0), ESMS 239 (MH$^+$)

(b) 1-(5-Iodopyridin-2-yl)-piperazine

To a solution of piperazine (215 mg, 2.5 mmol) and potassium carbonate (890 mg, 6.45 mmol) in acetonitrile (5 mL) was added 2-chloro-5-iodopyridine (300 mg, 1.25 mmol) (prepared in Example 2(a)). The mixture was heated at reflux for 26 h and allowed to cool. It was then filtered and the solvents removed under reduced pressure. Column chromatograpgy of the residue on silica gel (dichloromethane:methanol:ammonia solution 100:5:1) gave 1-(5-iodopyridin-2-yl)-piperazine as a yellow solid (215 mg, 60%). δH (300 MHz DMSO-$d_6$) 2.76 (4H, m, piperazinyl), 3.40 (4H, m, piperazinyl), 6.72 (1H, d, J=9.0), 7.77 (1H, dd, J=2.4 and 9.0), 8.25 (1H, d, J=2.4), ESMS 290 (MH$^+$)

(c) 3-[4-(5-lodopyridin-2-yl)-piperazin-1-yl]methyl-1H-pyrrolo[2,3-b]pyridine

To a solution of 1-(5-iodopyridin-2-yl)-piperazine (100 mg, 0.34 mmol) in toluene (2 mL) (prepared in Example 2(b)) was added 3-(N,N-dimethylaminomethyl)-1H-pyrrolo[2,3-b]pyridine (58 mg, 0.32 mmol) (prepared in Example 1(a)). The mixture was heated at reflux over night and then allowed to cool to room temperature. The resulting solid was filtered and dried in vacuo to give 3-[4-(5-iodopyridin-2-yl)-piperazin-1-yl]methyl-1H-pyrrolo[2,3-b]pyridine as a colourless solid (118 mg, 79%). δH(300 MHz DMSO-$d_6$) 2.47 (4H, m, piperazinyl), 3.45 (4H, m, piperazinyl), 3.68 (2H, s), 6.71(1H, d, J=9), 7.05 (1H, dd, J=4.8 and 7.9), 7.39 (1H, s), 7.75 (1H, d, J=8.8), 8.06 (1H, d, J=7.8), 8.21 (1H, d, J=4.5), 8.23 (1H, s), 11.51 (1H, br s, NH)

EXAMPLE 3: Preparation of 3-[4-(5-bromopyridin-2-yl)-piperazin-1-yl]methyl-1H-pyrrolo[2,3-b]pyridine (a) (5-Bromopyridin-2-yl)-piperazine A solution of 2,5-dibromo piperazine (1.59 g, 8 mmole), and piperazine(1.45 g, 16 mmole), and potassium carbonate (6 g) in acetonitrile (50 mL) was heated at reflux for 48 h. The heating was discontinued and the solution allowed to cool to room temperature. The solid was filtered off and washed with acetonitrile (50 mL). The organics were concentrated to a tan solid. The product was purified by column chromatography on silica gel using dichloromethane:methanol:triethylamine (94:5:1) as eluent to provide (5-bromopyridin-2-yl)-piperazine as an offwhite solid (1.75 g, 95%). δH (300 MHz CDCl$_3$) 1.75 (1H, br s), 2.95 (4H, m, piperaziny), 3.45 (4H, m, piperazinyl), 6.52 (1H, d, J=9.0), 7.51 (1H, dd, J=2.5 and 9.0), 8.17 (1H, d, J=2.4), ESMS 243 (MH$^+$).

(b) 3-[4-(5-Bromopyridin-2-yl)-piperazin-1-yl]methyl-1H-pyrrolo[2,3-b]pyridine

A solution of 1-(5-bromopyridin-2-yl)-piperazine (310 mg,1.28 mmol) (prepared in Example 3(b)) and 3-(N,N-dimethylaminomethyl)-1H-pyrrolo[2,3-b]pyridine (215 mg, 1.16 mmol) (prepared in Example 1(a)) in toluene (10 mL) was heated at reflux for 18 h. The heating was discontinued and the solution allowed to cool to room temperature during which time a colourless solid precipitated out of solution. The solid was collected by filtration and dried in vacuo to yield 3-[4-(5-bromopyridin-2-yl)-piperazin-1-yl]methyl-1H-pyrrolo[2,3-b]pyridine as a colourless solid (420 mg, 97%). δH (300 mhz CDCl$_3$) 2.58 (4H, m, piperazinyl), 3.51 (4H, m, piperazinyl), 3.75 (2H, s), 6.50 (1H, d, J=9.0), 7.09 (1H, dd, J=5.0 and 7.9), 7.27 (1H, s), 7.49 (1H, dd, J=2.6 and 9.0), 8.10 (1H, d, J=7.8), 8.17 (1H, d, J=2.3), 8.32 (4.5), 9.69 (1H, br s) ESMS 374 (MH$^+$)

EXAMPLE 4: Preparation of 1-t-butoxycarbonyl-3-[4-(5-bromopyridin-2-yl)-piperazin-1-yl]methyl-1H-pyrrolo[2,3-b]pyridine To a solution of 3-[4-(5-bromopyridin-2-yl)-piperazin-1-yl]methyl-1H-pyrrolo[2,3-b]pyridine (200 mg, 0.54 mmol) and KOH (91 mg, 1.6 mmol) in dichloromethane (2 mL) at room temperature was added di-tert-butyldicarbonate (130 mg, 0.59 mmol). The mixture was stirred at room temperature for 4 h and was then filtered. The residue was washed with dichloromethane and the solvents removed under reduced pressure. The resulting residue was purified by column chromatography on silica gel using ethyl acetate-:dichloromethane 7:3 as eluent to give the title compound as a colourless foam (230 mg, 91%). δH (300 MHz CDCl$_3$) 1.67 (9H, s); 2.58 (4H, m, piperazinyl); 3.51 (4H, m, piperzinyl); 3.6 (2H, s); 6.52 (1H, d, J=9.0); 7.19 (1H, dd, J=4.6 and 7.5); 7.51 (1H, dd, J=2.5 and 9.0); 7.54 (1H, s); 8.09 (1H, d, J=7.9); 8.18 (1H, d, J=2.5); 8.51 (1H, d, J=4.2)ESMS 472 (MH$^+$)

EXAMPLE 5: Preparation of 1-t-butoxycarbonyl-3-[4-(5-trimethylstannylpyridin-2-yl)-piperazin-1-yl] methyl-1H-pyrrolo[2,3-b]pyridine A mixture of 1-t-butoxycarbonyl-3-[4-(5-bromopyridin-2-yl)-piperazin-1-yl]methyl-1H-pyrrolo[2,3-b]pyridine (35 mg, 0.074 mmol), hexamethylditin (40 μL, 63 mg, 0.193 mmol), and tetrakis(triphenylphosphine) palladium (0) (25 mg, 0.022 mmol) in toluene (5 mL) under argon was heated at reflux for 3 h during which time the solution darkened to a very dark brown. Another portion of tetrakis (triphenylphosphine) palladium (0) (13 mg, 0.01 mmol) was added and the reaction refluxed for 5 h further. The heating was discontinued and the mixture allowed to cool to room temperature. The reaction was then filtered through a short pad of celite and the pad washed with ethyl acetate. The solvents were then removed under reduced pressure. The resulting black residue was purified by preparatory silica plate using ethyl acetate as eluent to give the semi-pure title compound as a colorless glass (20 mg, 48%). δH (300 MHz CDCl$_3$) 0.24 (9H, s, trimethylstannyl), 1.65 (9H, s, t-butoxycarbonyl), 2.56 (4H, m, piperazinyl), 3.52 (4H, m, piperazinyl), 3.64 (2H, s, CH$_2$), 6.61 (1H, d, J=8.3), 7.16 (1H, dd, J=4.8 and J=7.7), 7.43 (1H, m), 7.50 (1H, s), 8.16 (1H, s), 8.48 (1H, d, J=4.6), ESMS 558 (MH$^+$)

EXAMPLE 6: Preparation of $^{123}$I-1-t-butoxycarbonyl-3-[4-(5-trimethylstannylpyridin-2-yl)-piperazin-1-yl]methylpyrrolo[2,3-b]pyridine To a vial of sodium $^{123}$I iodide in sodium hydroxide was added in the following order: 20 μL acetic acid, 300–400 μg 1-t-butoxycarbonyl-3-[4-(5-trimethylstannylpyridin-2-yl) piperazin-1-yl]methylpyrrolo[2,3-b]pyridine in 100 μL ethanol, and 50 μg Chloramine T in 50 μL of distilled water. This mixture was swirled for 30 seconds and let stand at room temperature for 40 minutes. 20 uL 1N HCl was added and the reaction was let stand at room temperature for 30 minutes. Analysis and purification of the compound was carried out by HPLC on reverse phase C18 silica column using a gradient of 0 to 90% acetonitrile in water containing 0.1% trifluoroacetic acid over 20 minutes. The labeled $^{123}$I-3-[4-(5-iodopyridin-3-yl)-piperazin-1-yl]methyl-1H-pyrrolo[2,3-b]pyridine eluted with a retention time of 11.2 minutes and was shown to be the correct compound by coinjection with a reference sample of nonradioactive 3-[4-(5-iodopyridin-2-yl)-piperazin-1-yl]methyl-1H-pyrrolo[2,3-b]pyridine.

EXAMPLE 7: Receptor Binding Affinities

D2 and D4 receptor-binding affinities of the compounds prepared in Examples 1, 2 and 3 were evaluated as described in Grandy et al., 1989, *Proc. Natl. Acad. Sci*, 86:9762–9766 and Van Tol et al, 1992, *Nature*, 358:149–152 (the disclosures of which are hereby incorporated by reference) for their ability to reduce binding of $^3$H-spiperone as compared to the reference compound clozapine. The potency of the test compound to reduce $^3$H-spiperone binding is directly correlated to its binding affinity for the receptor.

The test compounds were assayed at a range of concentrations and the % inhibition of $^3$H-spiperone binding at each test concentration was measured. Specific binding in the absence of test compound is the difference of total binding minus non-specific binding and similarly specific binding (in the presence of test compound) is the difference of displacement binding minus non-specific binding. An inhibition response curve was used to determine the IC$_{50}$ of the test compound 3-[4-(5-iodopyridin-3-yl)-piperazin-1-yl] methyl-1H-pyrrolo[2,3-b]pyridine. Ki was calculated by the Cheng and Prustoff transformation:

Ki=C$_{50}$/(1+[L]/K$_D$)

where [L] is the concentration of $^3$H-spiperone used in the assay and K$_D$ is the dissociation constant of $^3$H-spiperone determined independently under the same binding conditions.

Assay results (Ki) are reported in the following Table 1, and % inhibition of $^3$H-spiperone binding at various concentrations (1 nM, 10 nM and 100 nM) of various test compounds are reported in Table 2. These results show clearly the D4 selectivity of compounds of the invention.

TABLE 1

| Compound | D4 Ki (nM) | D2 Ki (nM) |
|---|---|---|
| [structure: 3-[4-(5-iodopyridin-3-yl)-piperazin-1-yl]methyl-1H-pyrrolo[2,3-b]pyridine] | 1.0 | 3655 |
| [structure: 3-[4-(pyridin-2-yl)-piperazin-1-yl]methyl-1H-pyrrolo[2,3-b]pyridine] | 0.91 | 621 |

$^3$H-spiperone binding is directly correlated to its binding affinity for the receptor.

Briefly, the D4 receptor is utilized in the form of membrane preparations obtained from HEK 298 cells stably transfected with human D4 receptor (D4.2 sub-type). D2 receptor is utilized in the form of membrane preparations obtained from GH$_4$C$_1$ (rat pituitary) cells stably transfected with the human D2 receptor (short isoform). The total spiperone binding assay is started by the addition of 500 ml (50 mg protein) membrane homogenate to a solution of 900 ml incubation buffer and 100 ml (0.25 nM final conc.) $^3$H-spiperone. The binding reaction is stopped and the samples are filtered under vacuum and the filters are then washed 3 times with 5 ml ice cold 50 mM Tris buffer (pH 7.4). Individual filter disks are put in scintillation vials (Biovials, Bechman). Ready Protein Plus liquid scintillant (5 ml, Beckman) is added and the vials counted by liquid scintillation spectrophotometry (Beckman LSC 6500) after equilibrating for three hours at room temperature to determine total binding (B$_T$).

Non-specific binding for D4 is assayed by incubating membrane homogenate, $^3$H-spiperone and fresh dopamine. Filtrate is counted using the same procedure as in the total binding assay described above to give the non-specific binding value (NSB). Non-specific binding for D2 is similarly assessed, with the exception that (−)sulpiride is used in place of dopamine.

To assess displacement, membrane homogenate is incubated with $^3$H-spiperone and test compound dissolved in DMSO. Filtrate is counted using the same procedure as in the total binding assay described above, to give the displacement binding value (B$_D$).

The test compounds are assayed at a range of concentrations chosen such that the middle dose would cause about 50% inhibition of $^3$H-spiperone binding. Specific binding in the absence of test compound (B$_0$) is the difference of total binding (BT) minus non-specific binding (NSB) and similarly specific binding (in the presence of test compound) (B) is the difference of displacement binding (B$_D$) minus non-specific binding (NSB). IC$_{50}$ is determined from an inhibition response curve, logit-log plot of % B/B$_0$ vs concentration of test compound, and Ki can be calculated from this using the Cheng and Prustoff transformation as described above.

TABLE 2

| Compound | % Inhibition of binding to D4 at: | | | % Inhibition of binding to D2 at: | | |
|---|---|---|---|---|---|---|
| | 1 nM | 10 nM | 100 nM | 1 nM | 10 nM | 100 nM |
| [structure: 3-[4-(5-bromopyridin-2-yl)-piperazin-1-yl]methyl-1H-pyrrolo[2,3-b]pyridine] | 26 | 78 | 98 | <10 | <10 | <10 |

Alternatively, the D2 and D4 receptor-binding affinities of the compounds of the invention can be evaluated as described in WO95/17400 (the disclosure of which is hereby incorporated by reference) for their ability to reduce binding of $^3$H-spiperone as compared to the reference compound clozapine. The potency of the test compound to reduce

We claim:

1. A method of radioimaging a human brain, comprising the step of administering to a patient a radiopharmaceutical composition comprising a radiopharmaceutically acceptable carrier and a compound of Formula (I):

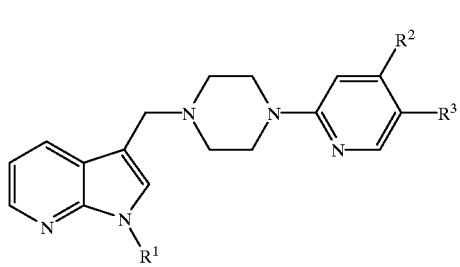 (I)

wherein
$R^1$ is selected from H and an acid labile protecting group; and
$R^2$ and $R^3$ are independently selected from H, radioisotopic halo, loweralkoxy and tri(loweralkyl)tin; and salts, solvates or hydrates thereof, one of $R^2$ and $R^3$ being radioisotopic halo, in an amount effective to image a human brain, allowing the radiopharmaceutical to localize within the brain, and then taking an image of the brain of the patient so treated.

2. A method of radioimaging a human brain, comprising the step of administering systemically to a patient a radiopharmaceutical composition comprising a radiopharmaceutically acceptable carrier and a compound of Formula (I):

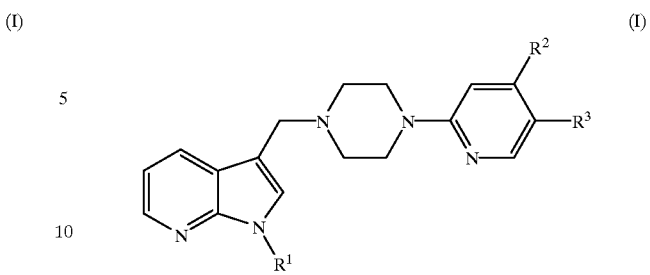 (I)

wherein
$R^2$ and $R^3$ are independently selected from H, radioisotopic halo,
$R^1$ is selected from H abnd an acid labile protecting group; and loweralkoxy and tri(loweralkyl)tin; and salts, solvates or hydrates thereof, one of $R^2$ and $R^3$ being radioisotopic halo, one of $R^2$ and $R^3$ being $^{123}I$, in an amount effective to image a human brain, allowing the radiopharmaceutical to localize within the brain, and then taking an image of the brain of the patent so treated.

* * * * *